United States Patent [19]

Purdy et al.

[11] 4,041,956
[45] Aug. 16, 1977

[54] PACEMAKERS OF LOW WEIGHT AND METHOD OF MAKING SUCH PACEMAKERS

[75] Inventors: David L. Purdy, Indiana; Vernon L. Speicher, Leechburg; Frederick J. Shipko, Spring Church; William L. Johnson, Kittanning, all of Pa.

[73] Assignee: Coratomic, Inc., South Indiana, Pa.

[21] Appl. No.: 658,737

[22] Filed: Feb. 17, 1976

[51] Int. Cl.² .............................................. A61N 1/36
[52] U.S. Cl. .............................................. 128/419 P
[58] Field of Search ....... 128/419 P, 419 PG, 419 PS, 128/421, 422; 219/121 L

[56] References Cited

U.S. PATENT DOCUMENTS

| | | | |
|---|---|---|---|
| 3,382,343 | 5/1968 | Muncheryan | 219/121 L |
| 3,842,842 | 10/1974 | Kenny et al. | 128/419 P |
| 3,866,616 | 2/1975 | Purdy et al. | 128/419 PS |
| 3,884,243 | 5/1975 | Cywinski | 128/419 PS |
| 3,888,260 | 6/1975 | Fischell | 128/419 P |
| 3,943,937 | 3/1976 | King et al. | 128/419 P |

*Primary Examiner*—William E. Kamm
*Attorney, Agent, or Firm*—Hymen Diamond

[57] ABSTRACT

A method of making a pacemaker which includes, in a container a subassembly of, a battery nested in an electrical converter serving to produce heart-pacing pulses. This subassembly is encapsulated in a mold in rigid, polyurethane foam of low weight and capable of protecting the encapsulated components from shock. The body formed by prepotting is generally ellipsoidal and is nested snugly in one of the sections of an ellipsoidal container. Another section of the container is welded to the one section along the congruent rims. Additional potting material is injected through the boards between the sides of the encapsulated body and the adjacent walls of the container. The encapsulated body is held firmly in the container without potting material between the top and bottom and ends of the body and the container. The potting material is injected through the hole in which the electrical feedthrough is subsequently welded. Alternatively, the pacemaker is formed by enclosing the subassembly between the parts of the container, welding the sections of the container, and injecting the foam through the opening in the container through which the output conductor passes.

23 Claims, 30 Drawing Figures

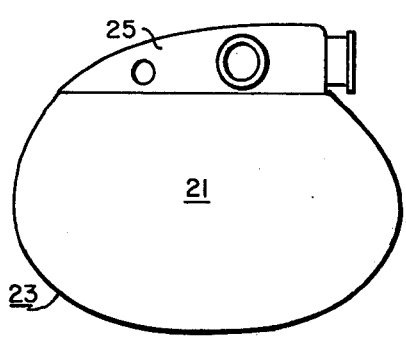
FIG. 1
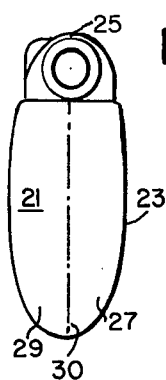
FIG. 1a
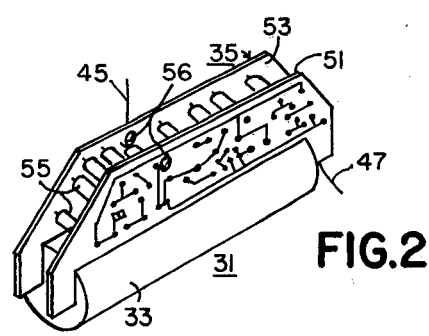
FIG. 2
FIG. 3
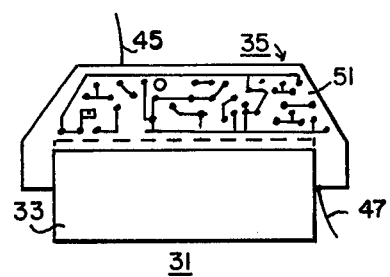
FIG. 4
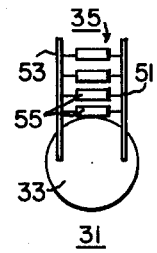
FIG. 5
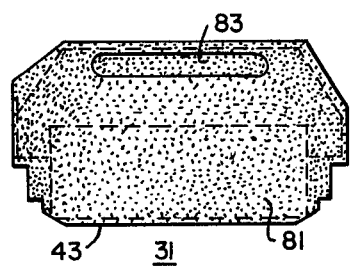
FIG. 6
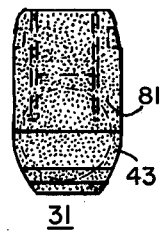
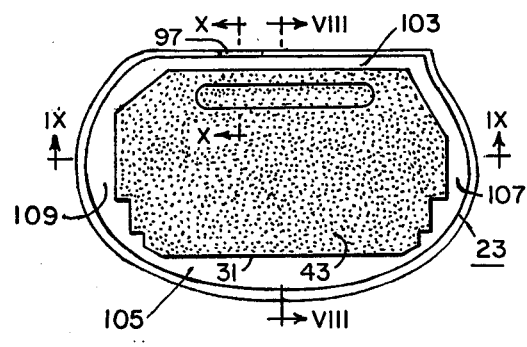
FIG. 7

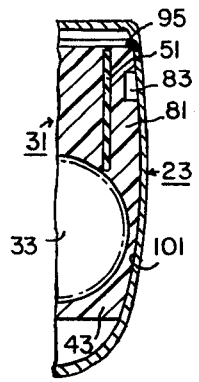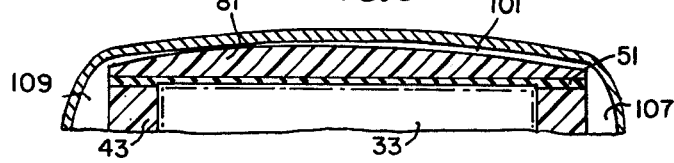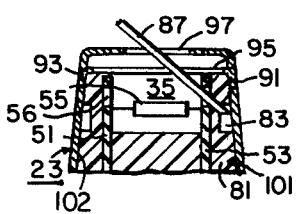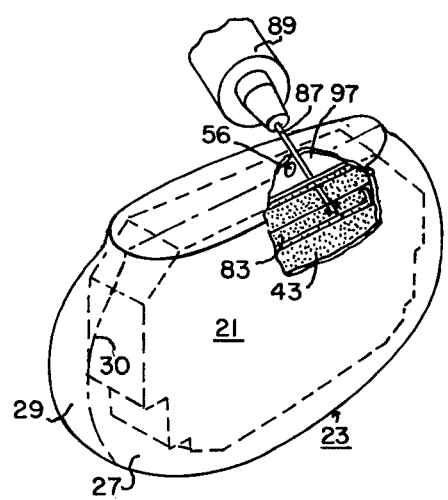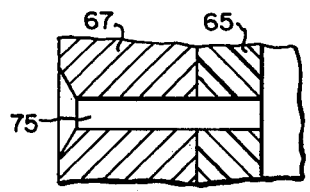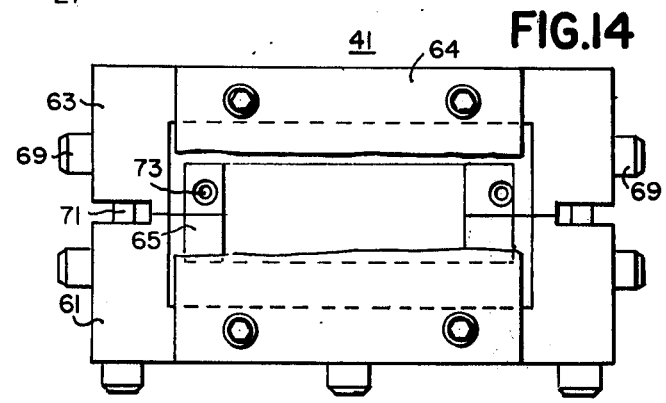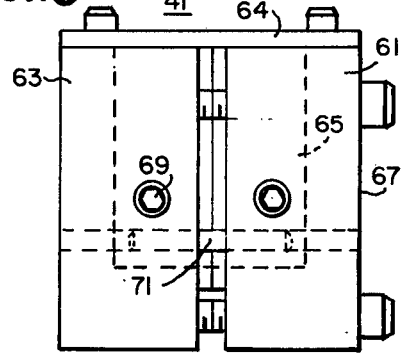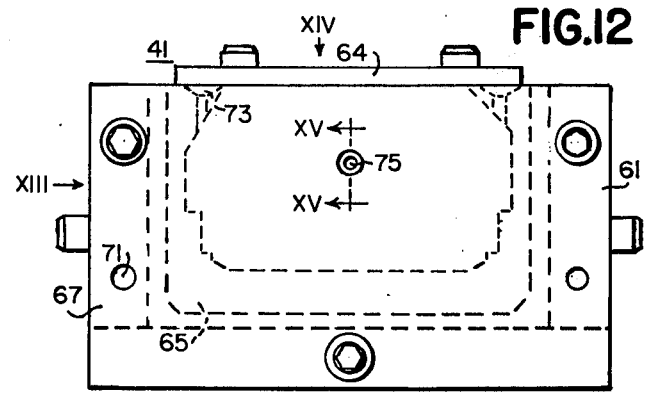

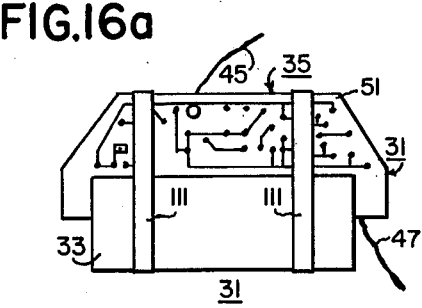
FIG.16a
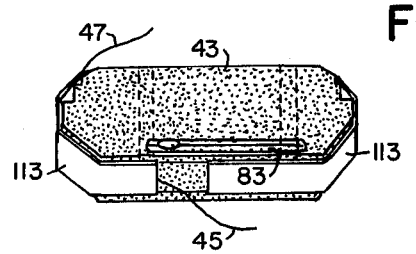
FIG.16c1
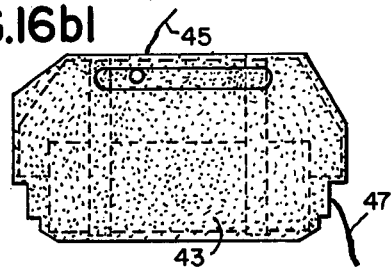
FIG.16b1
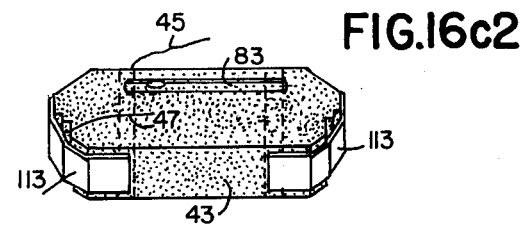
FIG.16c2
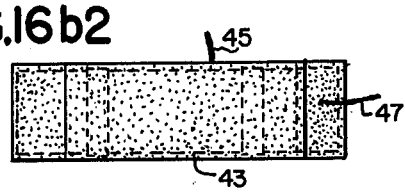
FIG.16b2
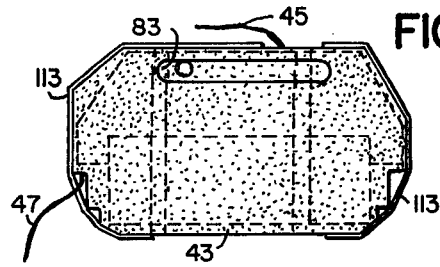
FIG.16c3
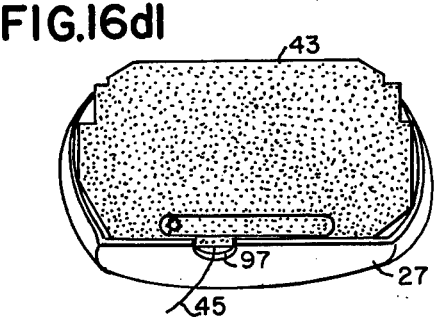
FIG.16d1
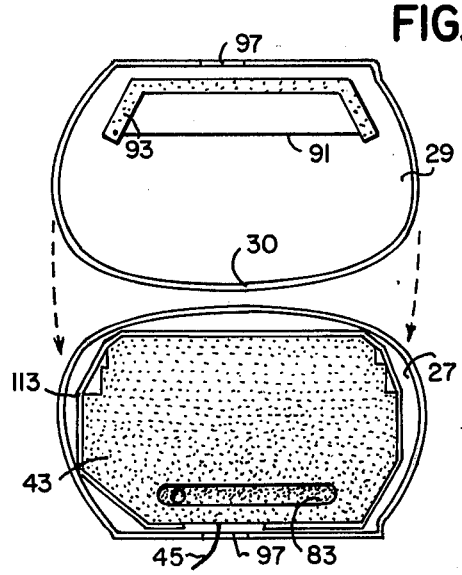
FIG.16d2

PACEMAKERS OF LOW WEIGHT AND METHOD OF MAKING SUCH PACEMAKERS

A pacemaker in which a subassembly of a converter and battery are encapsulated in low-weight rigid foam in a container. The encapsulation extends only between the sides of the subassembly and the container in one modification of the pacemaker.

BACKGROUND OF THE INVENTION

This invention relates to pacemakers and has particular relationship to implantable pacemakers. An implantable pacemaker includes a primary power source and a converter for converting the output of the source into pulses for the heart and for controlling the flow of pulses to the heart. The source and converter are enclosed in a container which is implanted typically in the left-hand portion of the chest or in the abdomen. The converter supplies its pulses to the heart through a catheter. It is desirable, if not indispensible, that the pacemaker be of as light-weight and of as low volume as practicable and it is an object of this invention to provide a light-weight and low-volume pacemaker.

Purdy et al U.S. Pat. No. 3,866,616 discloses an isotopic pacemaker having a primary source of radioactive material whose heat is converted into electricity by a thermoelectric unit. The source and the thermoelectric unit and a converter, including the control, are embedded in silicone rubber. Because the primary source is of very low mass, typically about one-third gram, this pacemaker is of light-weight and low-volume, typically sixty-seven grams and thirty-three cubic centimeters.

There are also pacemakers in which the primary power source is a battery. Recently pacemakers in which the primary source is a lithium battery and which is of relatively long life has come into vogue. Typically, in a lithium battery the electrolyte is lithium iodide and the anode is lithium and the cathode is a combination of lead iodide and lithium iodide. Typically, seven banks of three cells each in series, are connected in parallel delivering about six volts. The use of the parallel banks creates a seven-fold redundancy providing protection against failure of one or more cells. In pacemakers of this type, in accordance with the teachings of the prior art, the converter and battery is potted in EPOXY resin or the like. The potting serves to prevent the shocks, to which the pacemaker is subjected during the normal day-to-day movement and physical encounters of the host, from damaging the pacemaker. Such pacemakers have the disadvantage that their weight and the volume which they occupy is excessive.

It is an object of this invention to overcome the disadvantages of the prior art and to provide a method of making a light-weight, low-volume pacemaker whose components shall be embedded in potting which shall effectively prevent them from being damaged by shock. It is also an object of this invention to provide such a light-weight, low-volume pacemaker.

SUMMARY OF THE INVENTION

In accordance with this invention the weight and volume of a pacemaker are minimized in two principal ways: The primary source, converter and container are so related that the mass of potting material required to secure the pacemaker firmly in the container is minimized and the potting material is composed of a polymer foam, particularly polyurethane foam. The polyurethane foam is a light-weight material which is nonetheless affords adequate protection against shocks to the components of the pacemaker.

In the practice of this invention the pacemaker is made from components including the converter, the primary source and complementary open sections of a container whose openings are bounded by congruent rims. The converter includes spaced printed-circuit boards between which the electrical components of the converter are mounted. The boards and components are thus formed into a rigid body. The converter and source are engaged to form a subassembly. This subassembly is prepotted in a mold in a low-density potting material, such as polyurethane foam, to form a body which is capable of nesting snugly in one, or either, of the sections of the container. This body is then nested in the one section and this section then joined by welding to the other section to form the container. The potting extends only to the top of the printed-circuit-board body and the boards have openings which are drilled out after the potting. The welded container has a hole at the top through which the lead from the converter is brought out. Once the container is welded additional potting material is injected through the openings on each side of the printed-circuit-board potted body by a syringe or the like inserted through the hole in the container. The potted or encapsulated body is thus firmly secured in the container. The lead is then brought out through the feedthrough hole and the feedthrough is sealed about the hole. The sealing takes place typically by laser welding in a chamber which is evacuated and back filled with argon so that the assembly within the container and its potting are, when in use, in an atmosphere of argon.

Alternatively, the foam is injected after the container is formed with the subassembly of the battery and the converter contained in it. For this purpose the subassembly of the battery and the converter are nested in one of the sections of the container. The sections of the container are then welded together. The foam is injected through the opening in the welded container through which the output conductor passes.

In forming the rigid polyurethane foam an appropriate polyisocyanate and polymer-containing hydroxyl groups, both, in liquid form are injected into the mold or into the container, as the case may be, and the foam is formed. The foam is then cured. The pacemaker made in the practice of this invention has the ovaloid form of the pacemaker disclosed in Purdy U.S. Pat. No. 3,987,799. This invention has unique advantages in pacemakers in which the primary source is a battery. It also has advantages in isotopic pacemakers as disclosed in Purdy et al. U.S. Pat. No. 3,866,616 and to the extent that this invention is used in such pacemakers such use is within the scope of this invention.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 1 is a view in side elevation of a pacemaker in accordance with this invention and made in the practice of this invention;

FIG. 1a is a view in end elevation as seen in the direction 1a of FIG. 1.

FIG. 2 is a view in perspective of the subassembly of the printed-circuit board and battery of a pacemaker, as shown in FIG. 1, in which the primary source is a battery;

FIGS. 3 and 4 are views in side elevation and end elevation respectively of the subassembly, shown in FIG. 2;

FIGS. 5 and 6 are views in side elevation and in end elevation respectively of the subassembly shown in FIG. 2 after it is encapsulated in potting material;

FIG. 7 is a view in side elevation showing the prepotted body in FIGS. 5 and 6 nested in one of the complementary sections which form the container of the pacemaker shown in FIG. 1;

FIG. 8 is a fragmental view in section taken along line VIII — VIII of FIG. 7;

FIG. 9 is a fragmental view in section taken along line IX — IX of FIG. 7;

FIG. 10 is a fragmental view in section taken along line X — X of FIG. 7 and also showing the manner in which the additional potting material is injected;

FIG. 11 is a view in perspective showing the prepotted body in the container of the pacemaker and the manner in which the additional potting material is injected;

FIG. 12 is a view in side elevation of the mold in which the prepotted body is formed;

FIG. 13 is a view in end elevation of the mold shown in FIG. 12 taken from the direction of the arrow XIII of FIG. 12, FIG. 14 is a plan view of this mold taken in the direction of the arrow XIV of FIG. 12;

FIG. 15 is a fragmental view in section taken along line XV — XV of FIG. 12 and showing the injection hole for the foam-forming components;

FIGS. 16a 16b1, 16b2, 16c1, 16c2, 16c3, 16d1 and 16d2 are views of the subassembly of the battery and converter before potting and, in various positions, after potting and also of the container, the successive steps in producing a pacemaker in the practice of this invention; the components 39, 45, 272, 275, 277 are left unsectional in the interest of clarity.

DETAILED DESCRIPTION OF INVENTION

Figure 17:
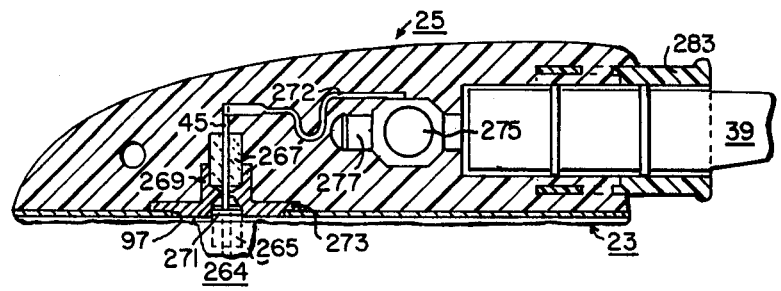
FIG. 17 is a fragmental view in section showing the head of the pacemaker through which the pulses are derived.

The apparatus shown in FIG. 1 and 1a is a pacemaker 21 including a container 23 typically of titanium or other material not rejected by the human body having a head 25 of transparent EPOXY resin through which the catheter 39 (FIG. 17) is connected to the converter 35. Typically, the overall length of this pacemaker is 2.53 inches; the overall width, 1.99 inches; and the overall thickness 0.760 inch. A pacemaker of these dimensions weighs about 70 grams and has a volume of forty-seven cubic centimeters and the ovaloid form of the pacemaker shown in Purdy U.S. Pat. No. 3,987,799. The container 23 is assembled of complementary side sections 27 and 29 (FIGS. 1a, 16d1, 16, 18) terminating in peripheral rims 30 which are congruent. The dimensions and weights given above are given only for the purpose of aiding those skilled in the art of practicing this invention and not with any intention of in any way limiting this invention.

Within the container 23 the pacemaker includes a subassembly 31 (FIGS. 2 - 4) including a battery 33 and a converter 35. The subassembly 31 is potted in potting material of a light-weight polymer foam. Polyurethane foam was found to highly satisfactory as it is of light-weight (low-density) and effectively protects the battery and the converter from shock. Foam is typically produced with catalyst 12 - 2H. — This catalyst produces a rigid foam having a density of two to three pounds per cubic foot — See Technical Bulletin 6-2-2A-ECCOFOAM FPH, Emerson & Cummings, Inc. Canton, Massachusetts. In addition to low-density, this foam has favorable dielectric properties suppressing currect leakage from the battery 33. Silicone rubber has a far higher density than the polyurethane foam. The ECCOSIL 2CN which is used in the heart pacer described in Purdy U.S. Pat. No. 3,866,616 (Col. 2, line 40) has a density of 0.99 grams per cubic centimeter or 61.81 pounds per cubic foot.

In the practice of the invention shown in FIGS. 1 through 17, the subassembly 31 is first potted in a mold 41 (FIGS. 12 through 15) to form a prepotted or encapsulated body 43 (FIGS. 5, 6). The prepotted body 43 is then nested in one section 27 (FIG. 16d2) of the container 23. Then the sections 27 and 29 are welded along the rim 30 to form the container 23. After the welding operation additional potting material is injected between the sides of the body 43 and the inner surfaces of the container 23.

The battery 33 is of circularly cylindrical shape. For long life a lithium battery is preferred. The converter 35 includes pulse forming and control networks. Since the battery 33 delivers about six volts, the DC-DC voltage converter 13 usually included in such apparatus is dispensed with. The converter 35 has an output terminal 45.

The converter 35 includes spaced parallel printed-circuit boards 51 and 53 on which the conductors (FIG. 16a) of the circuits of the converter are printed. The electronic components 55, the transistors, diodes, resistors, capacitors, etc. of the converter 35 are mounted between the boards 51 and 53. The components 55 and the boards 51, 53 are so constituted into a rigid structure, albeit it may be deformed by the bending of the wires connected to the components 55 to the boards. The components 55 are secured below the tops of the boards 51 and 53 as shown in FIGS. 2 and 4 and there are openings 56 in the boards near the top.

The boards 51 and 53 and the converter 35 are of generally C-configuration. The battery 33 is nested between the legs of the boards and abuts the inner surface of the converter.

The subassembly 31 is formed into the body 43 by prepotting in mold 41 (FIGS. 12 through 15). The mold 41 is formed by abutting and bolting together mold sections 61 and 63 to form a cavity. The cavity is provided with a cover plate 64 which is provided with an opening (not shown) for emission and removal of excess foam. Each section 61 and 63 is composed of metal such as aluminum and has liner 65 of non-electrically conducting EPOXY resin (HYSOL 4351) which internally has the form of the surface of body 43. The liner 65 is included to preclude short-circuiting of the battery 33. Each section 61 and 63 has walls 67 defining a generally rectangular internal space. A male preform is inserted in the opening of each section and the EPOXY resin is poured into the space between the preform and the walls defining the space. When the EPOXY resin hardens and sets the preform is removed laterally from the space. So that, if necessary, the liner 65 may be removed, the walls of the space are covered with a silicone oil before the EPOXY resin is deposited. The resin is held by bolts 69 which penetrate into the liner 65 and may be removed when the liner 65 is to be removed. The sections 61 and 63 of the mold which are abutted and bolted are aligned by pin 71 which extends into both sections. A plurality of holes 73 and 75 are provided in the top of the mold and in its side walls for injecting the liquid for producing the foam. The holes 73 in the top penetrate through the EPOXY resin into the cavity and are accessed through holes (not shown) in the cover 64. The resin injected into these holes 73 in the form of liquid supplies the foam to the top of converter 35 which is the foam potting the components 55. The holes 75 penetrate through the metal walls 67 of the mold and through the EPOXY resin 65. The entrance to the holes 73 and 75 are countersunk as shown in FIG. 15.

In producing the prepotted body 43, the subassembly 31 is inserted in one of the parts 61 or 63 of the mold 41 and then the parts are bolted together to form the cavity occupied by the subassembly. A rubber plug (not shown) is inserted in the top of the subassembly between the boards 51 and 53 to prevent the penetration of foam into this region. The output conductor 45 is placed in this region when the prepotted body is assembled in the container. The prepotted body 43 is thus produced. This body has a layer (FIG. 10) of foam on its outer surface and the components 55 are also immersed in foam below the region where the plug is inserted. The layer 81 is provided with slots 83 (FIGS. 10, 16c2) extending across the top of the side of body 43. These slots provide an attenuated region in the body through which the needle 87 of the syringe 89 (FIGS. 10 and 11) which injects the additional foam is inserted. A hole is drilled through the foam wall of the slot 83 for this purpose.

The body 43 is nested in one section 27 of the container 23 (FIGS. 16d1, 16d2). But before the nesting the section 27 and 29 are provided with cooperative parts 91 and 93 (FIGS. 10, 16d2) of a gasket for preventing the penetration of foam into the upper portion of the container 23 when the additional foam is injected. Each of these parts 91 and 93 includes a strip of polyimide sheet (KAPTON) having a strip of polyurethane rubbery foam on its surface secured near the tops of the sections 25, 27. After the gasket parts are secured to the container sections 27 and 29, the body 43 is nested in the section 27 and the sections 27 and 29 are brought together with the congruent rims 30 in coincidence and the joint between the rims 30 is welded. The container 23 is formed. When the sections 27 and 29 are brought together the gasket sections 91 and 93 are compressed as shown in FIG. 10 and a barrier 95 to the penetration of foam is formed above the potting layer 81.

The container 23 includes an opening 97 (FIG. 7, 10, 11, 17) for the feedthrough output wire 45 from the converter 35. There are very narrow spaces 101 and 102, typically of about .013 inch between the outer surface of the layer 81 (body 43) and the inner surfaces of the sections 27 and 29 of the container 23 (FIGS. 8, 9, 10). The spaces 103 and 105 (FIG. 7) between the top and bottom of the body 43 and the container 23 and the spaces 107 and 109 (FIG. 7) between the ends of the body 43 and the container 23, which are left void, are substantially greater and may be as high as one-fourth inch. The body 43 is held in the container 23 by the injection of foam into the narrow spaces 101 and 102.

The foam is injected in the spaces 101 and 102 by the syringe 89. The needle 87 of the syringe 89 penetrates through the opening 97, the holes 56 on one side and then the other and the slots 83 and injects the liquid which forms the foam into the spaces 101 and 102. The reaction which forms the foam produces a large volume of gas which produces high pressure overcoming the capillary forces of the spaces 101 and 102 and enabling the chemical components which form the foam to penetrate into the spaces 101 and 102. The body 43 is thus securely fastened to the inner wall of container 23.

The steps in producing the part of the pacemaker 21 less the head 25 which is thusfar described are presented in FIGS. 16a through 16d2.

As shown in FIG. 16a the converter 35 and the battery 33 are assembled with the battery 33 nested between the legs of the converter 35 abutting its center portion. The subassembly is held together by strips 11 of glass tape wrapped about the converter 35 and battery 33 and secured by an adhesive.

The subassembly 31 shown in FIG. 16a is prepotted in mold 41 producing the body 43. A side view of the body 43 in the same orientation as in FIG. 16a is shown in FIG. 16b1 and a top view is shown in FIG. 16b2. In prepotting or encapsulating the subassembly 31 the liquid which forms the foam is injected by a hypodermic syringe in the holes 73 and 75 of the mold 41. There are typically about five or six such holes, each about one-sixteenth inch in diameter, into which the hypodermic needle is inserted. Before molding, the mold is heated to about 50° C. Foaming takes place in the mold 41 in about one minute. Excess foam escapes through the hole (not shown) in the top 64. After the foaming the mold and its contents is heated at 50° C for about sixteen hours to cure the foam.

The sections 27 and 29 of the container 23 are welded around their congruent rims 30 by electron-beam or laser welding. Laser welding has the advantage that it can be carried out under pressure in an inert atmosphere. In the practice of this invention, the welding is carried out in argon at about one atmosphere pressure or higher. The inert atmosphere is used to prevent vaporization of the titanium of the container 23 during the welding and also to prevent contamination of the weld by out-gassing.

To protect the encapsulated body 43 and its components a shield 113 of copper, typically about 0.005 inch thick, is adhered by an epoxy adhesive to the ends and sides of the body 43 in regions where the parts vulnerable to the heat of the welding beam are located. Copper is highly effective as a shield against a laser beam. There should be sufficient space between the weld zone and the copper to assure that the weld is not contaminated by the copper or the potting material.

FIGS. 16c1, 16c2, 16c3 show the molded body with in place this shield 113. FIG. 16c1 is a view taken from above the body lying on its side with the top of the body 43 (where the hole 97 is) so that it appears at the bottom of the photograph. FIG. 16c2 is a like view with the body 43 reversed and FIG. 16c3 is a view taken from the side of the body.

The encapsulated body prepared as disclosed above is nested in the section 27 of the container 23 as shown in FIG. 16d1. To accomplish this purpose it is essential that the cavity of the mold 41 be dimensioned so that the molded body 43 has the proper dimensions for nesting in the section 27. FIG. 16d2 shows the sections 27 and 29 of the container 23 before the sections are aligned with their rims 30 in contact and welded. When the sections 27 and 29 are squeezed together preparatory to welding, the parts 91 and 93 of gasket (FIGS. 10, 16d2) form a seal on the three sides of each section 27 and 29 in the upper portion of the container. This seal prevents the resin injected in the holes 56 from escaping over the top and sides of the body 43 and assures that the resin is forced into the spaces 101 and 102.

Before the container is sealed off the rim of the feedthrough hole 97 (FIGS. 10, 11) is milled. During this operation the deposit of chips on the body 43 is prevented by inserting rubber polyurethane foam in the cavity. The structure of the head 25 is similar to that shown in FIGS. 2 and 3 of Purdy et al. U.S. Pat. No. 3,866,616.

The output conductor 45 is initially connected into a feedthrough assembly 264 (FIG. 17). This assembly includes a ferrite radio-frequency filter 265 which suppresses electro-magnetic disturbances and which encircles the conductor 45. The assembly also includes a ceramic insulating sleeve 267 through which the conductor 45 is sealed gas-tight. The sleeve 267 is sealed into a flanged sleeve 269, typically of titanium. The ferrite trap 265 is secured to the inner side of the flanged sleeve 269 by a spring washer 271. The conductor 45 is connected near its external end to a flexible connector 272. The assembly 264 is disposed adjacent the opening 97 with the flanges 273 of sleeve 269 appropriately positioned adjacent the hole 261. In an atmosphere of inert gas the flange 273 is lap welded to the rim of the hole 97 sealing the hole. The connector 272 is now connected to the terminal block 275. The terminal block 275 is in the form of a rectangular parallelapiped having a cylindrical opening through which the inner end 277 of the catheter 39 passes. Laterally a set screw (not shown) is provided in the block 275. Over the head of the set screw there is a silicone rubber plug (not shown). The catheter 39 is inserted in heart pacer 21 by the doctor who installs it in the host's heart. During the construction of the pacer 21 the catheter 39 is replaced by a pin (not shown) of the diameter of the catheter 39, encircled by a suture boo 283.

The pacer as now assembled is mounted in a mold (not shown), and the head 25 formed of transparent EPOXY resin.

Figure 18:
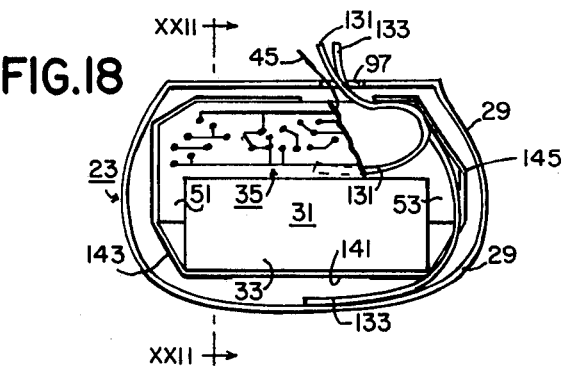
FIG. 18 is a view in side elevation of a container containing the subassembly including the converter and battery, showing the practice of a modification of this invention.
Figure 19:
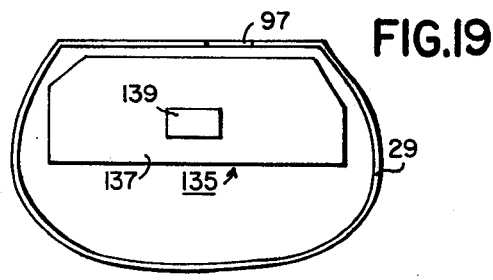
FIG. 19 is a view in side elevation of a complementary section of the container of the modification shown in FIG. 18 showing the manner in which each section of the container is prepared for assembly.
Figure 20:
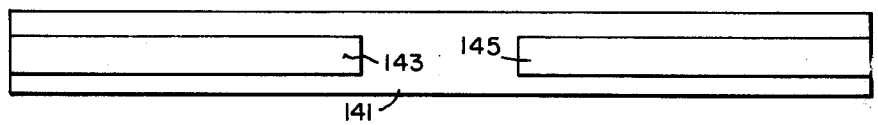
FIG. 20 is a plan view of the welding shield, developed, for the assembly of the modification shown in FIG. 18.

In the practice of the modification of the invention shown in FIGS. 18 through 22, the prepotting is eliminated. the subassembly 31 secured by glass tape 111 (FIG. 16a), which is not shown, in FIG. 18, in the interest of clarity, is in this case nested in one of the complementary sections 25 or 27 of the container 23 and the rigid foam is diposited through thinwalled silicon-rubber tubes 131 and 133. Tube 131 passes through the opening 97 (FIG. 18) for feedthrough conductor 45, then around the outside at one end of the boards 51 and 53, but between the boards, and then through the space between the boards under the components 55 (FIG. 2) secured to the boards. The tube 133 passes through opening 97 also around the outside at one end of the converter 31 and the battery 33, between the boards 51 and 53, and terminates under the battery approximately centrally of the lower end of the assembly 31. The foam components are injected through the tubes 131 and 133 and through the tubes are preferably removed before the foam forms and solidifies.

The following steps are followed in practicing the modification of the invention:

1. Composite strips 135 (FIGS. 21, 22) are prepared each of which includes polyimide sheet 137 near the center of which a block 139 of rubbery polyurethane foam is secured. Each sheet 137 is substantially congruent to each board 51 and 53.

2. Each strip 135 is secured in a complementary section 25 and 27 of the container 23, with the block 139 inwardly in a position such that when the subassembly 31 is between the sections, the boards 51 and 53 of the subassembly coincide with the sheet 137.

3. The subassembly 31 is nested in one section 25 or 27.

4. The tubes 131 and 133 (FIG. 18) are positioned with reference to the subassembly 31 as described above.

5. A weld shield (FIG. 20) is prepared. This weld shield includes a strip 141 of polyimide sheet along the longitudinal center of which strips 143 and 145 of copper are secured. Typically, the strip 141 is 5.75 inches long and 0.05 inches wide. The strips 143 and 145 are 0.25 inches wide. Separate discontinuous strips are used instead of one continuous strip to minimize weight. In the alternative a single strip of copper may be secured to sheet 141, the strip of copper extending under the battery 31.

Figure 21:
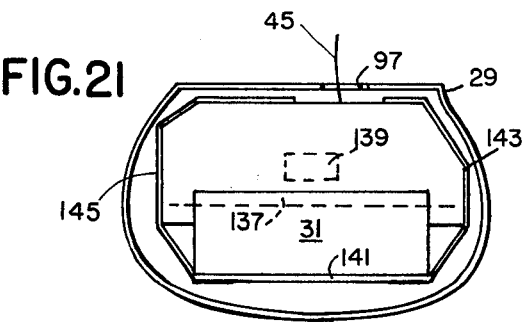
FIG. 21 is a view in side elevation of a container containing the subassembly of the converter and battery showing the disposition of the weld shield; shown in FIG. 20
Figure 22:
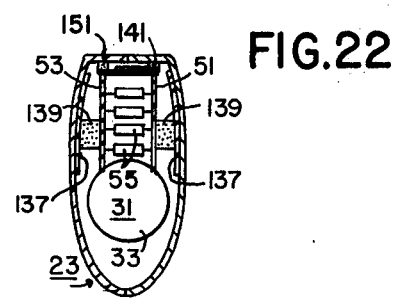
FIG. 22 is a view in section taken along line XXII-XXII of FIG. 18 with components 33 and 45 left unsectioned in the interest of clarity.

6. The weld shield is positioned around the periphery of the nested subassembly 31, shielding the tubes 131 and 133 in addition to the components 31, shielding the tubes 131 and 133 in addition to the components 55 of the subassembly 31 and the ends of the battery 33. The strips 143 and 145 respectively extend from the edges of the opening 97 to about one-quarter inch from the ends of the battery 33 (FIG. 21). Between the ends of the strips 143 and 145 (FIG. 21) the battery is spaced a substantial distance from the rim 30 of the container 23 and is not subject to damage by the welding. The strip 141 which carries the strips 143 and 145 is positioned edgewise in the section 25 or 27 of the container 23 and is not secured to the subassembly 31 or the container section.

7. The other complementary section is positioned with its rim 30 coincident with the rim of the section in which the subassembly is nested. The blocks 139 (FIG. 22) engage the boards 51 and 53 and center the subassembly 31 and the subassembly is insulated from the container 23. The complementary sections 25 and 27 engage the strip of polyimide 141 and hold this strip firmly away from the rim 30 which is the weld zone. To prevent the subassembly from skewing, it may be desirable to insert spacers 151 between the ends of the boards 51 and 53 and the tops of the container sections 25 and 27.

8. The sections 25 and 27 are joined pressure tight by butt welding starting at one edge of the hole 97, continuing around rims 30, and terminating at the other edge of hole 97. Prior to the welding, the ends of the tubes 131 and 133 and the wire 45 which protrude from the opening 97 are anchored to the sides of the sections 25 and 27 away from the weld zone.

9. The required quantity of the components which form the foam are injected into each tube 131 and 133 after the assembly is preheated to about 50° C. Heating enhances the foaming. To inject the components a hypodermic syringe containing the components is connected to each tube 131, 133.

10. The tubes 131 and 133 need not be withdrawn, but in the interest of minimizing weight, they are withdrawn immediately after the components are injected and before the foaming starts. The foaming starts about one minute after injection and in a short time fills the void space in the container 23. Excess foam flows out through the opening 97.

11. After the foam hardens but before it is cured (about fifteen minutes after injection) the excess foam is scraped from the container surface and is removed from the container 23 below the hole 97 to create a small cavity for conductor 45.

12. The foam is cured by heating the assembly at about 50° C for sixteen hours.

13. The output wire 45 if it is not already in the cavity, is placed in the cavity and the hole 97 is plugged with rubber-foam sponge. Metal chips produced during the milling operation, which follows, are prevented from dropping into the cavity.

14. The boundary of the hole 97 is milled.

15. The wire 45 is joined to the feedthrough connection (See FIG. 17).

16. Flange 261 is welded to the milled boundary of the opening 97.

17. The pacemaker is completed as described above.

While preferred embodiments and preferred practice of this invention are disclosed herein, many modifications thereof are feasible. This invention is not restricted except insofar as is necessitated by the spirit of the prior art.

We claim:

1. The method of making a pacemaker of parts including a primary power source, an electrical converter, and open complementary sections of a container whose openings are bounded by substantially congruent rims, the said method comprising, engaging said source and converter to form a subassembly, prepotting said subassembly to provide a body of dimensions such that it nests in one of said sections, said prepotted body having opening means permitting injection of additional potting material on at least one wall thereof, nesting said body in said one section, joining said one section and said other complementary section along said congruent rims to form said container, and injecting potting material through said opening means to substantially fill the space between said one wall and said section.

2. The method of claim 1 wherein the converter includes a plurality of generally parallel printed-circuit boards between which the electrical components of said converter are mounted, said boards and components being combined into a structure of generally C-section from which the ends extend on each side as legs and wherein the subassembly is formed by inserting the source between said legs so that it abuts the center portions of the circuit boards.

3. The method of claim 1 wherein the container is of generally ellipsoidal form, each complementary section of the container being in the form of a semi-ellipsoid, and wherein in prepotting the subassembly a generally ellipsoidal body is formed which nest in at least one of said sections and wherein after the joining of the section, potting material is injected between each side-wall of the body and the adjacent section of the container to fill the space between each said side wall and said adjacent section of said container.

4. The method of claim 1 wherein the prepotting material and the potting material is a polymer foam.

5. The method of claim 1 wherein the converter includes a plurality of spaced printed-circuit boards between which the electrical components of said converter are mounted and the source engages said boards on one side thereof and wherein in prepotting the subassembly of the converter and source the prepotting material is deposited over the source and the sides of the boards and between the boards to pot said components but said prepotting material is not deposited over the end of the converter opposite the source.

6. The method of claim 1 wherein the sections of the container are so formed as to provide a hole therein through which conductor means to be connected to a catheter are brought out and wherein the additional prepotting material is injected by means inserted into the openings in the prepotted body through said hole.

7. The method of claim 1 wherein the complementary sections are joined by welding with a laser beam.

8. The method of claim 7 wherein the welding takes place in an inert atmosphere at substantial pressure.

9. The method of claim 7 wherein the prepotted body is shielded from the laser beam.

10. The method of claim 9 wherein the shielding is effected by a strip of copper secured to the body.

11. The method of claim 1 wherein the complementary sections are joined by welding and the prepotted body is shielded from the heat of the welding.

12. The method of making a pacemaker of parts including a primary power source, an electrical converter, and open complementary sections of a container whose openings are bounded by substantially congruent rims, the said method comprising engaging said source and converter to form a subassembly, nesting said subassembly in one of said sections, joining said one section and said other complementary section along said congruent rims to form said container, said container having an opening in one side thereof, said subassembly extending between said one side and the side of said container opposite said one side, disposing said container vertically with said side containing said opening uppermost and said opposite side lowermost, inserting tube means in said opening so that its open end extends into said container adjacent said subassembly, and injecting a potting compound through said tube means to pot said subassembly in said container.

13. The method of claim 12 wherein a pair of tubes are inserted, said opening, one tube terminating within said converter below the components thereof and the other terminating below the subassembly.

14. The method of claim 12 wherein the potting material is a polymer foam.

15. The method of making a pacemaker of parts including a primary power source, an electrical converter, and open complementary sections of a container whose openings are bounded by substantially congruent rims, each of said sections including inwardly projecting means, the said method comprising, engaging said source and converter to form a subassembly, nesting said subassembly in one of said sections, joining said one section and said other complementary section along said congruent rims to form said container, with said inwardly projecting means centering said subassembly between said sections, said container following this joining and centering step including substantially no potting material therein and after said container is formed, injecting potting material through said opening means to pot said subassembly within said container and to secure said subassembly to said container.

16. The method of making a pacemaker of parts including a primary power source, an electrical converter, and open complementary sections of a container, each of said sections having inwardly projecting means, the said method comprising nesting said source and converter in one of said complementary sections, joining said complementary sections to form said container with said source and converter within said container, centered by said inwardly projecting means, said container containing substantially no potting material after this joining and centering step, said container having an opening in one side thereof, said source and converter extending between said one side of said container and the side of said container opposite said one side, and after said container is formed, injecting a potting material through said opening into said container to pot said source and converter in said potting compound.

17. The method of making a pacemaker of parts including a primary power source, an electrical converter, and open complementary sections of a container, each of said sections having inwardly projecting means, the said method comprising nesting said source and converter in one of said complementary sections, joining said complementary sections to form said container with said source and converter within said container, centered by said inwardly projecting means, said container containing substantially no potting material after this joining and centering step, said container having an opening in one side thereof, said source and converter extending between said one side of said container and the side of said container opposite said one side, and after said container is formed injecting liquid components which react to form a potting compound through said opening into said container to form said potting compound to pot said source and converter in said potting compound.

18. The method of claim 17 wherein tubes are inserted through the opening into the container, the ends of the tubes within the container extending about the source and converter at different points thereof and the liquid components are injected through said tubes.

19. A pacemaker of low weight including a primary power source, an electrical converter and a container, the source and converter being enclosed in said container potted in a light-weight potting material, the converter and source and the potting forming a body, potting material extending between the sides of said body and said container, there being void spaces between the upper and lower surfaces of said body and said container and between the ends of said body and the container.

20. The pacemaker of claim 19 wherein the converter includes a plurality of printed-circuit boards between which the electrical components of the converter are mounted, said printed-circuit boards and components forming a body of C-configuration from which the ends of the C extend as legs, the source being mounted between said legs and extending to the center portion of the C, the potting extending only over the source and the sides of the converter which extend from the source.

21. A pacemaker of low weight for supplying pulses to the heart of a host including a container and a subassembly within said container, said subassembly including a primary source and a converter cooperatively connected to supply said pulses, said subassembly being potted within said container in a light-weight potting material which is capable of protecting said converter and said battery from shock.

22. The pacemaker of claim 2 wherein the potting material is polyurethane foam.

23. The pacemaker of claim 21 wherein the converter includes generally parallel printed-circuit boards between which the electrical components of the converter are mounted and connected, the printed-circuit board being of generally C-section so that the converter is of generally C-section, the source being nested in the assembly in the space between the legs and the cross member of the C.

* * * * *

UNITED STATES PATENT AND TRADEMARK OFFICE
CERTIFICATE OF CORRECTION

PATENT NO. : 4,041,956

DATED : August 16, 1977

INVENTOR(S) : David L. Purdy

It is certified that error appears in the above-identified patent and that said Letters Patent is hereby corrected as shown below:

Column 12, claim 21, line 36, "battery" should read

-- primary source --.

Column 12, claim 22, line 37, "2" should read -- 21 --.

Signed and Sealed this

Sixteenth Day of September 1986

[SEAL]

Attest:

Attesting Officer

DONALD J. QUIGG

Commissioner of Patents and Trademarks